United States Patent [19]
Brungraber

[11] Patent Number: 5,576,478
[45] Date of Patent: Nov. 19, 1996

[54] PORTABLE TESTER FOR MEASURING SLIP RESISTANCE

[76] Inventor: Robert J. Brungraber, 1900 Fourth Ave./POB 387, Spring Lake, N.J. 07762

[21] Appl. No.: 519,705

[22] Filed: Aug. 28, 1995

[51] Int. Cl.⁶ .................................................. G01N 19/02
[52] U.S. Cl. .................................................................. 73/9
[58] Field of Search ........................................ 73/7, 9, 10

[56] References Cited

U.S. PATENT DOCUMENTS

| | | | |
|---|---|---|---|
| 4,759,209 | 7/1988 | Brungraber | 73/9 |
| 5,259,236 | 11/1993 | English | 73/9 |

*Primary Examiner*—Robert Raevis
*Attorney, Agent, or Firm*—Jacobson, Price, Holman & Stern, PLLC

[57] ABSTRACT

A portable apparatus for testing slip resistance of surfaces such as floors and bathtub surfaces operated by applying a pad of friction material to the surface and instantaneously applying a load to the pad at a selected angle. The load is applied by releasing a weight carried atop an articulated linkage on the bottom of which the friction pad is attached. The linkage slides in a frame which can be set at selected angles on a base, and a trigger bar mounted in the frame interacts with a rod of the articulated linkage to hold and release the weight.

12 Claims, 3 Drawing Sheets

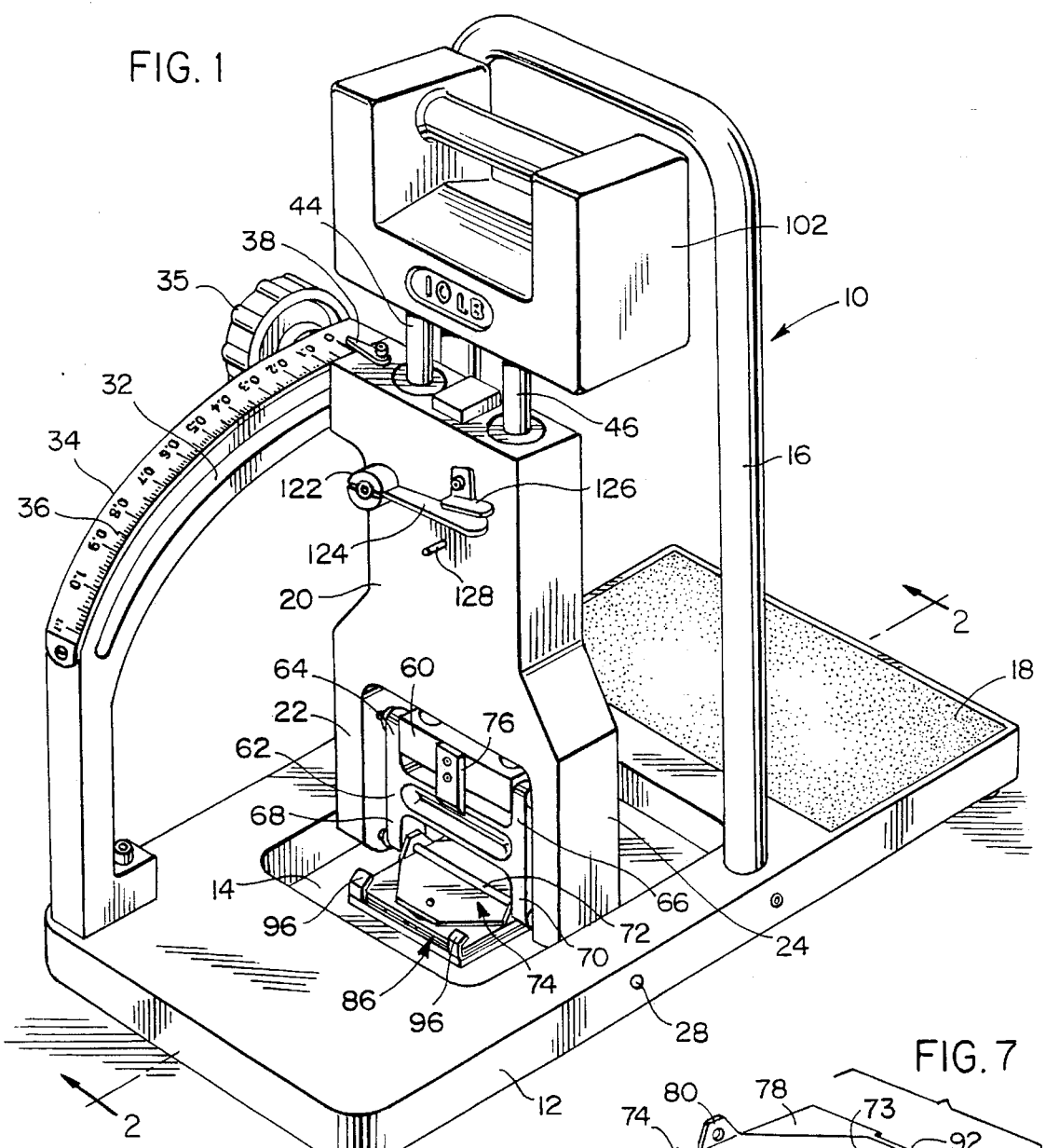
FIG. 1
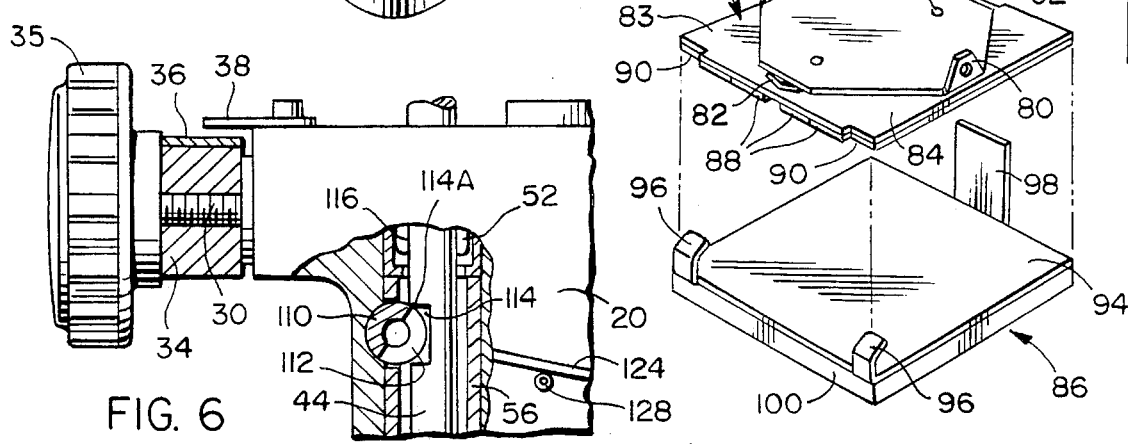
FIG. 6
FIG. 7

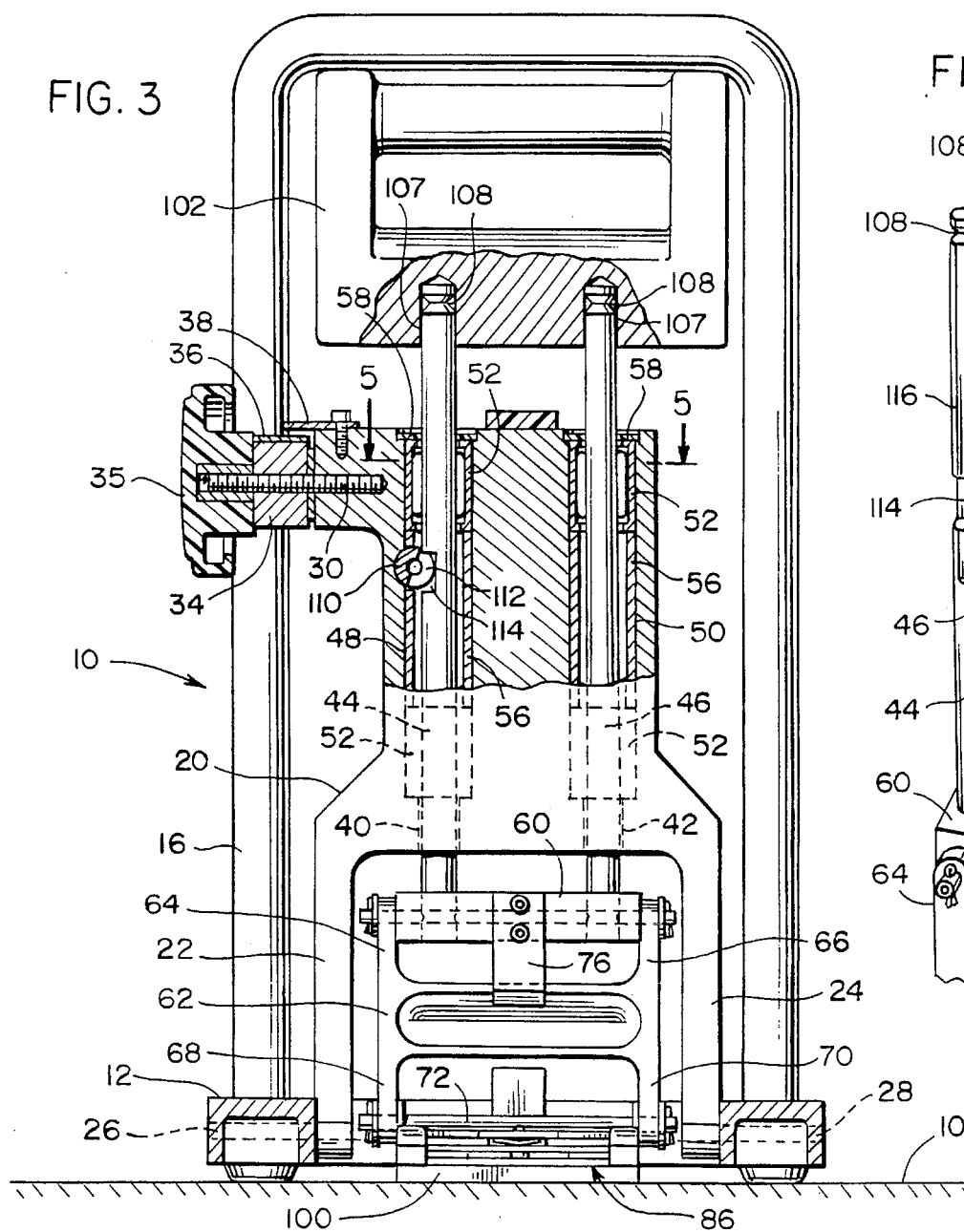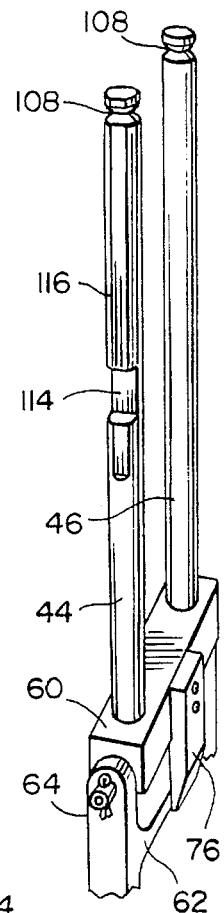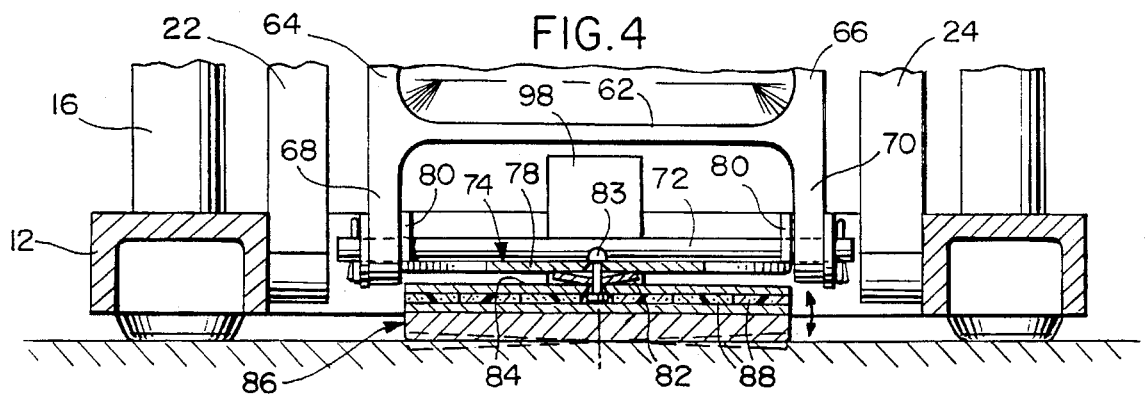

5,576,478

PORTABLE TESTER FOR MEASURING SLIP RESISTANCE

BACKGROUND OF THE INVENTION

This invention relates to an apparatus for testing or measuring the slip resistance (static coefficient of friction) of surfaces such as floors, bathtubs and the like.

For example, industry standards are established for minimum friction coefficients that are acceptable in commercial flooring or bathtub interiors. In order to test such surfaces, these standards may be related, in the former case to the coefficient of friction as between the flooring surface and a material representative of a shoe sole, and in the latter case to the coefficient of friction as between the bath tub surface and a material representative of human skin simulating the sole of the foot. Further, it is desirable for testing purposes, to have apparatus available which can be readily transported from site to site in order to test floor, bathtub and like surfaces for slip resistance, rather than having to submit a surface sample to a laboratory for testing.

Over the years, numerous different machines have been proposed for testing surface friction or slip resistance. Applicant's prior U.S. Pat. No. 4,759,209, for example, incorporated herein by reference, discloses a portable test apparatus which includes an articulated linkage having at the bottom a foot plate with a foot pad of test material which rests on a surface to be tested, the apparatus including means for setting the linkage at selected angles and applying a load substantially instantaneously to the linkage at a selected angle to determine whether the pad will slip on the test surface at the selected angle.

The apparatus includes an upright frame carrying the articulated linkage, the frame being pivotally mounted on a base and being supported for movement along a part-circular segment disposed in a vertical plane. The frame is movable along the segment into selected angles to the vertical so as to pre-establish an angle of attack for the articulated linkage relative to the test surface. The top link of the articulated linkage comprises rods which extend through and project upwardly from the frame. A weight is carried at the top of the rods and a releasable trigger is provided between the top of the frame and the weight to hold the linkage with the foot pad slightly above a surface being tested in a slightly elevated position when the trigger is set and to substantially instantaneously allow the linkage to drop when the trigger is released. If the angle of the linkage is sufficiently shallow, the pad will slip on the test surface when the linkage is released. The trigger comprises an L-shaped lever, the horizontal limb of which is pivoted on the top of the frame. The top of the vertical limb engages the bottom of the weight when the trigger is set, and manually pivoting the lever disengages the vertical limb from the weight to release the trigger. Some effort is needed, however, to frictionally drag the top of the lever across the bottom surface of the weight to release the trigger.

SUMMARY OF THE INVENTION

The present invention provides a portable slip resistance tester of the kind disclosed in the '209 patent, but which has an improved, more positively acting and mechanically sound trigger mechanism for instantaneously applying load to the articulated linkage.

According to the invention, the rods of the articulated linkage again extend through and project upwardly from a frame which can be set at selected angles on a baseplate and the upper ends of the rods carry a weight or are provided with other load-applying means. The lower ends of the rods are connected through a pivot or elbow joint to a foot-plate assembly for attaching a pad of test material. In this invention, however, the improved trigger mechanism includes a transverse trigger bar or tube journalled in the frame on an axis immediately adjacent one of the rods of the articulated linkage. There is a notch in the rod and a corresponding notch in the trigger bar with the configuration being such that the notches can be brought into register by vertical adjustment of the rods and the trigger bar can be swivelled about its axis into a position in which it interferes with the rod, and the upper shoulder of the notch in the rod engages the outer periphery of the trigger bar at a point adjacent its notch to form a stop for the rods. The linkage in this position, is somewhat elevated and supported by the trigger bar. A slight swivelling movement of the trigger bar from this position, however, causes the notch in the trigger bar to clear the upper shoulder of the notch in the rod providing an instantaneous transfer of the load of the weight from the trigger bar to the articulated linkage and allowing the foot-plate to drop onto a test surface. To provide clearance for the trigger bar and allow downward movement of the rods in cases where the foot pad slips and the articulated linkage bends at its elbow joint, the rod which is provided with the notch has an elongate flat on its periphery extending upwardly somewhat from the notch. To swivel the trigger bar between its respective positions, it may be provided with a collar on the outside of the frame with a radially outwardly projecting finger tab.

The invention also provides an improved foot pad attachment which provides for lateral tilting movements of the foot pad to accommodate irregularities and the like in surfaces being tested.

BRIEF DESCRIPTION OF THE DRAWINGS

FIG. 1 is a perspective view of a portable slip tester according to the invention;

FIG. 3 is a sectional view on line 3—3 of FIG. 2;

FIG. 4 is an enlarged front elevational view, partly in section, of a foot plate assembly of the apparatus;

FIG. 6 is an enlarged front elevational view, partly in section of an upper part of the apparatus.

FIG. 7 is an exploded perspective view of parts of the foot plate assembly; and

FIG. 8 is a perspective view of parts of an articulated linkage used in the apparatus.

DETAILED DESCRIPTION OF THE PREFERRED EMBODIMENTS

Figure 2:
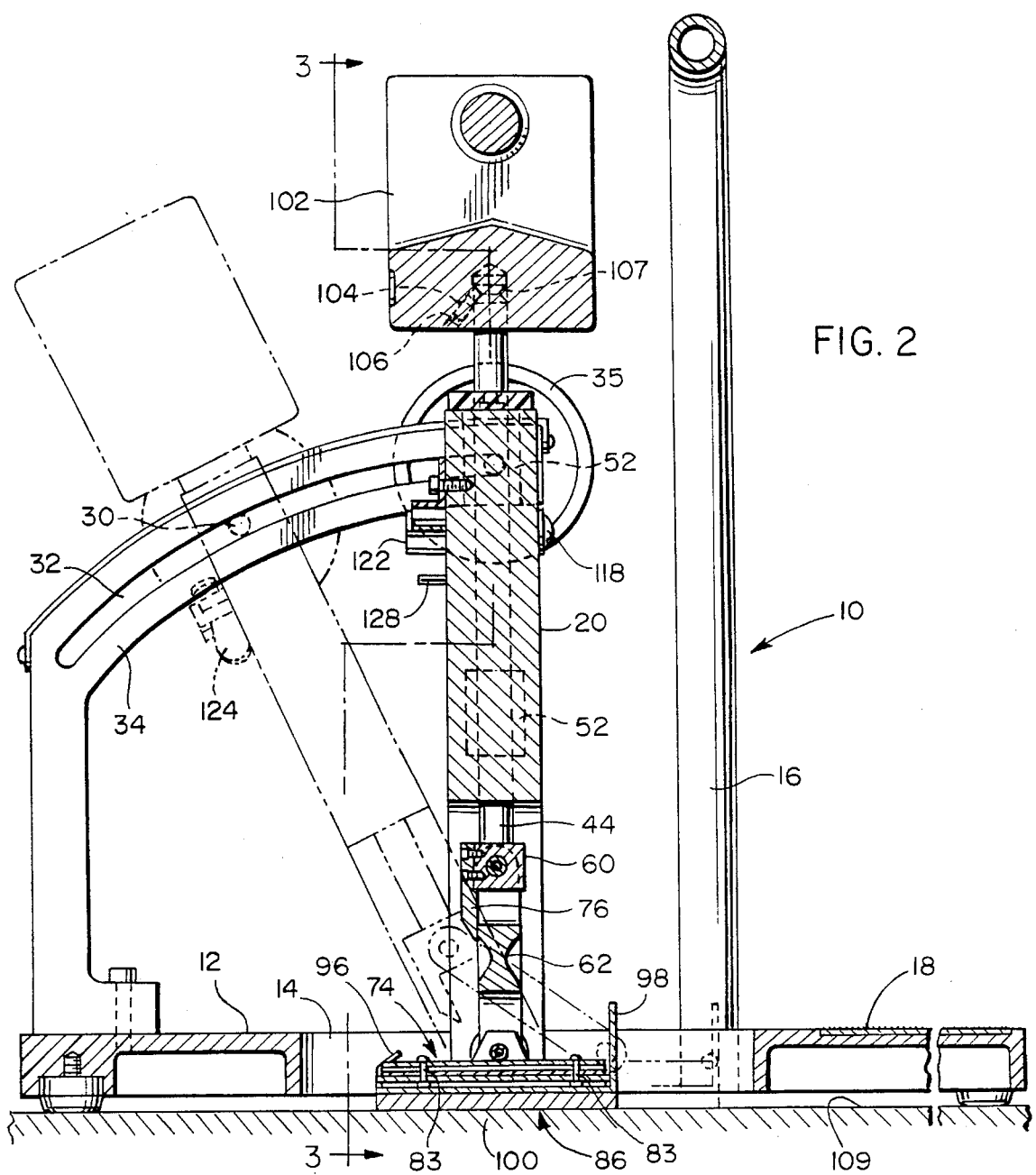
FIG. 2 is a side elevational view of the apparatus shown partly in section.
Figure 5A:
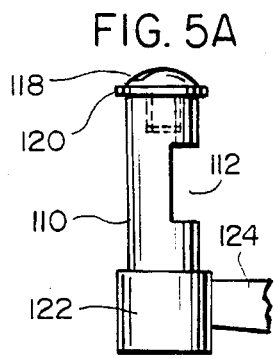
FIG. 5A is a plan view of a trigger bar.
Figure 5:
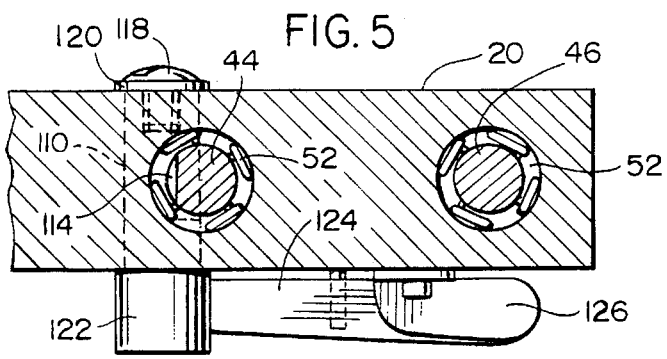
FIG. 5 is a sectional view on line 5—5 of FIG. 3.

The portable testing apparatus 10 shown in the drawings has a planar support base 12 with a central rectangular aperture 14, an upright U-shaped carrying handle 16 and a covering 18 on which an operator can place a foot to stabilize the apparatus in use.

A metal frame 20 has a bifurcated lower end forming legs 22, 24 and the legs are pivotally attached to the base on opposite sides of aperture 14 by pivot pins 26, 28. The upper end of frame 20 has a projecting screw 30 received in a track 32 of a segment plate 34 supported on the base. A knob 35 threads onto the end of screw 30 and against the side of the segment plate to fix frame 20 at a selected angle relative to the vertical. The segment plate has a graduated angle scale 36 and the frame 20 has a pointer 38 to indicate its angle.

Frame 20 has parallel vertical bores 40, 42 to receive rods 44, 46 of an articulated linkage as will be described, the bores 40, 42 opening into larger counter-bores 48, 50 (see FIG. 4) extending to the top of frame 20. In each counterbore are positioned a pair of linear ball bushings 52 separated by spacer tubes 56. At the top, each counterbore is closed off by a dust cap 58. The linear ball bushings provide for smooth movement of the rods 44, 46 in the frame 20.

At their bottom ends, rods 44, 46 are attached to a cross-bar 60 which is pivotally connected to a yoke-like element 62 having upper limbs 64, 66 pivoted to the cross-bar 60 to form an elbow joint and lower limbs 68, 70 pivotally connected by a pin 72 to a foot plate assembly 74. An articulated linkage is thus defined by the rods 44, 46 (upper link) the yoke-like element 62 (central link) and the foot plate assembly 74 (lower link). The cross-bar 60, carries a stop 76 for the yoke-like element 62 so that folding of the elbow-joint can only take place in one direction.

Foot plate assembly 74 comprises an upper plate 78 with ears 80 by which it can swivel on pin 72, a V-shaped plate 82 and a lower plate 84. The V-shaped plate 82 and the lower plate 84 are secured to the upper plate 78 by headed pins 83 with sufficient clearance that the V-shaped plate allows the lower plate to tilt or swivel laterally somewhat as shown by the small arrow in FIG. 4. This provides accommodation to irregular test surfaces for a foot pad assembly 86 to be releasably attached to the foot plate assembly. The under surface of lower plate 84 of the foot plate assembly carries an array of permanent magnets 88 and the plate has front and back recesses 90, 92.

Foot pad assembly 86 comprises an upper metal plate 94 with upwardly projecting front and back tabs 96, 98 adapted to be received in recesses 90, 92 and a pad 100 of test material, simulative of human skin or shoe sole material for example, adhered to the lower surface of plate 94. It is evident that foot pad assembly attaches releasably to the foot plate assembly by magnetic attraction being positively located in position by the tabs 96, 98. The apparatus may be provided with two or more foot pad assemblies with pads 100 of different materials respectively.

The swivelling structure provided by the V-shaped plate 82 is somewhat simplified and more economical than the structure disclosed in the aforesaid patent in which inclined surfaces are formed on the upper plate itself.

The rods 44, 46, at their upper ends are received in openings 107 in a load-applying weight 102, for example a 10 lb weight. The weight is releasably attached to the rods by screws 104 in inclined threaded bores 106 provided in the weight, so that the ends of the screws can engage in peripheral grooves 108 at the top of the rods to secure the weight in place.

The frame 20 is provided with a trigger mechanism, as will now be described, for holding the rods 44, 46 in an elevated position with the foot pad 100 clear of a surface 109 being tested and for substantially instantaneously releasing the rods allowing the pad to drop onto the surface under the influence of weight 102 and slide along the surface (as indicated by the dotted lines in FIG. 2) if the frame 20 is at a sufficiently shallow angle.

The trigger mechanism comprises a lateral trigger bar 110, in this case of tubular form, which is rotatably carried in a suitable bore formed in frame 20 so that the axis of bar 110 is offset somewhat from the axis of rod 44. The diameters of bar 110 and rod 44 and the inter-axis spacing is such that the bar and rod would normally interfere. Bar 110 however is formed with a notch 112 and a corresponding notch 114 is formed in rod 44. Also, the rod 44 is machined to provide a flat 116 extending upwardly from notch 114 on the side of rod 44 which faces the trigger bar.

As seen in FIG. 3 for example, the trigger bar 110 can be swivelled about its axis to a position in which notch 112 provides clearance for rod 44 and the rods 44, 46 are thus free to slide in frame 20. When notch 114 in rod 44 is brought into alignment with the trigger bar, however, the trigger bar can be swivelled clockwise about its axis to the position shown in FIG. 6 where a point on the outer periphery of the trigger bar engages under the top shoulder 114A of notch 114 to form a stop preventing downward sliding movement of the rods 44, 46 in frame 20. The location of notch 114 in rod 44 is such that in the stopped position of the rods, foot pad 100 is suspended slightly above the test surface 109 in all angles of frame 20. Then, rod 44 can be released to operate the apparatus by counter-clockwise swivelling of bar 110 from the FIG. 6 postion.

The trigger bar 110 is held in place at one end by a thread-in screw 118 with a washer 120. At its other end the trigger bar has a collar 122 with a radially extending finger tab 124 used to swivel the trigger bar in the counterclockwise direction from the FIG. 6 position by squeezing the tab 124 towards a fixed tab 126 on the outside of frame 20, the tabs fitting conveniently between an operators thumb and forefinger. After completion of a test, weight 102 is lifted manually to raise the rods 44, 46 and when notches 112, 114 become re-aligned the trigger bar will be returned to the FIG. 6 position by gravity due to the weight of tab 124 so that the linkage is once again held in the elevated position ready for the next test. A stop 128 is provided for the tab on the outside of frame 20.

It is evident that the trigger mechanism provides an effective and mechanically elegant means for holding the linkage in the elevated position and for substantially instantaneously applying the load to the foot plate when required.

While only a preferred embodiment of the invention has been described herein in detail, the invention is not limited thereby and modifications can be made within the scope of the attached claims.

I claim:

1. A portable apparatus for testing slip resistance of a surface comprising an articulated linkage having upper and lower pivotally interconnected links, the upper link comprising a pair of elongated rods, a foot plate assembly pivotally interconnected to the lower link for supporting a foot pad of friction material to be applied to the surface to be tested, a frame having bores slidably receiving each of said rods, support means for setting the frame at selected angles relative to the surface to be tested, load applying means for applying a downwardly directed load to the articulated linkage at a selected angle of the frame; and trigger means having a set position for restraining the linkage from moving under the influence of said load applying means, the trigger means being manually movable out of said set position for releasing the linkage and providing substantially instantaneous application of said downwardly directed load to the linkage, wherein the trigger means includes a trigger bar mounted in said frame about a trigger axis disposed transversely to and adjacent a longitudinal axis of one of the rods, and said trigger bar and said one rod having respective formations which are engageable and disengageable by swivelling movements of said trigger bar about the trigger axis for moving said trigger means into and out of the set position.

2. Apparatus as claimed in claim 1 wherein the respective axes of said one rod and said trigger bar are spaced so as to provide relative interference between said one rod and said trigger bar, wherein said one rod and said trigger bar include respective alignable notches, wherein said respective formations on said trigger bar and said one rod comprise a part of said trigger bar peripherally adjacent the notch in said trigger bar and an upper shoulder of the notch in said one rod under which said part of said trigger bar can engage and disengage.

3. Apparatus as claimed in claim 2 wherein said one rod has a flat extending upwardly from the notch in said one rod to provide clearance for said trigger bar upon release of said trigger means.

4. Apparatus as claimed in claim 1 wherein said trigger bar is provided with a collar outside said frame and a radially extending finger tab on the collar to swivel said trigger bar.

5. Apparatus as claimed in claim 4 including a fixed finger tab on the frame towards which said radially extending finger tab can be moved to release said trigger means by squeezing the tabs between thumb and forefinger.

6. Apparatus as claimed in claim 1 wherein the load applying means comprises a weight atop said rods.

7. Apparatus as claimed in claim 1 including linear ball bushing means in said bore for guiding said rods.

8. Apparatus as claimed in claim 1 wherein the support means comprises a base on which the frame is pivotally supported, a segment bar supported on the base and releasable securement means between the frame and the segment bar for clamping the frame against the bar at selected angles of the frame.

9. Apparatus as claimed in claim 1 wherein the foot plate assembly comprises an upper plate pivotally connected about a generally horizontally extending pivot axis to the lower link, a V-shaped plate under the upper plate having an apex extending generally horizontally and at right angles to the pivot axis connecting said upper plate to said lower link, a lower plate under the V-shaped plate, and pin means interconnecting the upper plate, the V-shaped plate and the lower plate for rocking movement of the lower plate about said apex of said V-shaped plate, the lower plate having attachment means for a foot pad assembly which includes said foot pad.

10. A portable apparatus for testing slip resistance of a surface comprising an articulated linkage having upper and lower pivotally interconnected links, the upper link comprising a pair of elongated rods, a foot plate assembly pivotally interconnected to the lower link for supporting a foot pad of friction material to be applied to the surface to be tested, a frame having bores slidably receiving each of said rods, support means for setting the frame at selected angles relative to the surface to be tested, load applying means for applying a downwardly directed load to the articulated linkage at a selected angle of the frame; and trigger means having a set position for restraining the linkage from moving under the influence of said load applying means, the trigger means being manually movable out of said set position for releasing the linkage and providing substantially instantaneous application of said downwardly directed load to the linkage, wherein the foot plate assembly comprises an upper plate pivotally connected about a generally horizontally extending pivot axis to the lower link, a V-shaped plate under the upper plate having an apex extending generally horizontally and at right angles to the pivot axis connecting said upper plate to said lower link, a lower plate under the V-shaped plate, and pin means interconnecting the upper plate, the V-shaped plate and the lower plate for rocking movement of the lower plate about said apex of said V-shaped plate, the lower plate having attachment means for a foot pad assembly which includes said foot pad.

11. Apparatus as claimed in claim 10 wherein the attachment means includes an array of permanent magnets on an under surface of the lower plate.

12. Apparatus as claimed in claim 10 wherein the attachment means includes peripheral recesses in the lower plate for receiving upstanding locator tabs on the foot pad assembly.

* * * * *